(12) United States Patent
Hansen

(10) Patent No.: US 6,926,893 B1
(45) Date of Patent: Aug. 9, 2005

(54) MULTI-STAGE CASCADE BOOSTING VACCINE

(75) Inventor: Hans J. Hansen, Mystic Island, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 09/688,089

(22) Filed: Oct. 16, 2000

Related U.S. Application Data

(60) Continuation of application No. 09/138,287, filed on Aug. 21, 1998, now Pat. No. 6,132,718, which is a division of application No. 08/268,129, filed on Jul. 6, 1994, now Pat. No. 5,798,100.

(51) Int. Cl.[7] ............................................. A01N 63/00
(52) U.S. Cl. ................. 424/93.7; 424/93.2; 424/93.71; 424/130.1; 424/131.1; 536/23.4
(58) Field of Search ...................... 536/23.4; 424/93.2, 424/93.7, 93.71, 130.1, 131.1

(56) References Cited

U.S. PATENT DOCUMENTS 5,874,540 A  2/1999 Hansen et al.
6,132,718 A  * 10/2000 Hansen .................... 424/131.1

FOREIGN PATENT DOCUMENTS

WO  15322  * 9/1992

OTHER PUBLICATIONS

Wagner et al, Biotechnology Therapeutics, vol. 3 p. 81 (1992).*
Eshhar et al PNAS, vol. 90 p. 720 (Jan. 1993).*
Hansen et al, Cancer vol. 71 p. 3478 (1993).*
Losman et al. Int. J. Cancer vol. 56 p. 580 (1994).*
Riott et al Immunology, 3rd Edition, pp. 7.8-7.14 (Mosby, 1993).*

* cited by examiner

*Primary Examiner*—Sheela J. Huff
(74) *Attorney, Agent, or Firm*—Heller Ehrman LLP

(57) ABSTRACT

Humoral and cellular immune responses against tumor cells and infectious agents are induced in a mammal using a vaccine comprising antibodies and anti-idiotype antibodies that mimic an epitope of antigen that is associated with a tumor or infectious agent. Antibodies and cytokines also may be used to amplify the immune cascade. Moreover, antibodies and anti-idiotype antibodies can be used to produce T cells that are not MHC-restricted and that are targeted to tumor cells and infectious agents.

6 Claims, No Drawings

MULTI-STAGE CASCADE BOOSTING VACCINE

This application is a continuation of application Ser. No. 09/138,287, filed Aug. 21, 1998, now U.S. Pat. No. 6,132,718, which is a divisional of application Ser. No. 08/268,129, filed Jul. 6, 1994, now U.S. Pat. No. 5,798,100.

BACKGROUND OF THE INVENTION

1. Field of the Invention

The present invention relates to methods for inducing humoral and cellular immune responses against malignant cells and infectious agents. In particular, this invention is directed to methods for producing an integrated immunologic response against tumor cells or infectious agents using antibodies and anti-idiotype antibodies that mimic an epitope of an antigen that is associated with a tumor or infectious agent. The present invention also is directed to a method for augmenting such an integrated response using antibodies and cytokines. This invention is further directed to methods for producing T cells that are not MHC-restricted, and that are targeted to a tumor associated antigen or an antigen associated with an infectious agent.

2. Background

One of the major goals of immunotherapy is to harness a patient's immune system against tumor cells or infectious organisms. With regard to cancer therapy, the objective is to direct the patient's immune system against tumor cells by targeting antigens that are associated with tumor cells, but not normal counterparts. Although these tumor associated antigens (TAA) have been difficult to identify, certain tumor cells express antigens that are normally not expressed, or expressed at very low levels, in adult life but present during fetal development. One example of such oncofetal TAA is α-fetoprotein, which is expressed by liver cancer cells. Another oncofetal TAA is the carcinoembryonic antigen (CEA), which is expressed in most adenocarcinomas of entodermally-derived digestive system epithelia, as well as in breast tumor cells and non-small-cell lung cancer cells. Thomas et al., *Biochim. Biophys. Acta* 1032: 177 (1990).

The administration of anti-idiotype antibodies (Ab2) mimicking TAA represents one of the most promising approaches to cancer immunotherapy. Goldenberg, *Amer. J. Med.* 94: 297 (1993). Ab2 are antibodies directed against the variable regions of conventional antibodies (Ab1). Since Ab2 and antigen can bind with the same regions of the Ab1-combining site, certain Ab2 (termed "Ab2β" or "internal-image" antibodies) can mimic the three dimensional structure of the nominal antigen. Jerne et al., *EMBO J.* 1: 243 (1982); Losman et al., *Int. J. Cancer* 46: 310 (1990); Losman et al., *Proc. Nat'l Acad. Sci. USA* 88: 3421 (1991); Losman et al., *Int. J. Cancer* 56: 580 (1994). Individuals immunized with Ab2β can develop anti-anti-antibodies (Ab3), some of which (Ab1') can bind the nominal antigen.

The antigen mimicry properties of anti-idiotype antibodies have led to the use of Ab2β as surrogate antigens (or idiotype vaccines), when the nominal antigen is not readily available or when the host is tolerant to the nominal antigen. In experimental systems, immunization with Ab2β mimicking certain TAA creates specific immunity to the TAA and protect against subsequent tumor growth. See, for example, Nepom et al., *Proc. Nat'l Acad. Sci. USA* 81: 2864 (1984); Raychaudhuri et al., *J. Immunol.* 139: 271 (1987). Similarly, anti-idiotype vaccines have been developed against infectious organisms, such as *Streptococcus pneumoniae* [McNamara et al., *Science* 226: 1325 (1984)], hepatitis B virus [Kennedy et al., *Science* 223: 930 (1984)], *Escherichia coli* K13 [Stein et al., *J. Exp. Med.* 160: 1001 (1984)], *Schistosomiasis mansoni* [Kresina et al., *J. Clin. Invest.* 83: 912 (1989)], and Moloney murine sarcoma virus [Powell et al., *J. Immunol.* 142: 1318 (1989)].

Cancer patients receiving an anti-TAA of animal origin will usually produce antibodies to the Ab1 and these anti-immunoglobulin antibodies include Ab2. Herlyn et al., *J. Immunol. Methods* 85: 27 (1985); Traub et al., *Cancer Res.* 48: 4002 (1988). The anti-idiotype response also may include the generation of T cells (T2). Fagerberg et al., *Cancer Immunol. Immunother.* 37: 264 (1993). Moreover, Ab2 may subsequently induce a humoral and cellular anti-anti-idiotypic response, Ab3 and T3, respectively, which may recognize the same epitope as Ab1. *Id.*

Thus, an opportunity exists to provide an approach to immunotherapy utilizing both humoral and cellular immune systems. The applicant has developed methods to provoke an integrated response against tumor cells, as well as against infectious agents. Furthermore, the applicant has developed methods to amplify the immune cascade.

SUMMARY OF THE INVENTION

Accordingly, it is an object of the present invention to provide a method for inducing humoral and cellular immune responses against tumor cells and infectious agents using antibodies and anti-idiotype antibodies that mimic a tumor associated antigen or an antigen that is associated with an infectious agent. It is a further object of this invention to provide a method to amplify such an integrated response using antibodies and cytokines.

Another object of this invention is to provide methods for producing T cells that are targeted to cells that express a tumor associated antigen or an antigen that is associated with an infectious agent. Such T cells are used to further augment the immune response against tumor cells or infectious agents.

These and other objects are achieved, in accordance with one embodiment of the present invention by the provision of a method for inducing humoral and cellular immune responses in a mammal against a tumor that expresses a tumor associated antigen (TAA) or against a disease caused by an infectious agent, comprising the steps of:

(a) administering a first vaccine to the mammal, wherein the first vaccine comprises an antibody component that binds with the TAA or with an antigen associated with the infectious agent, and wherein the antibody component is conjugated with a soluble immunogenic carrier protein; and (b) administering a second vaccine to the mammal, wherein the second vaccine comprises an anti-idiotype antibody component that mimics an epitope of the TAA or the infectious agent antigen, and wherein the anti-idiotype antibody component is conjugated with a soluble immunogenic carrier protein.

The antibody component of step (a) may be selected from the group consisting of: (a) a murine monoclonal antibody; (b) a humanized antibody derived from a murine monoclonal antibody; (c) a human monoclonal antibody; and (d) an antibody fragment derived from (a), (b) or (c), wherein the antibody fragment may be selected from the group consisting of F(ab')$_2$, F(ab)$_2$, Fab', Fab, Fv, sFv and minimal recognition unit.

Moreover, the anti-idiotype antibody component of step (b) may be selected from the group consisting of: (a) a polyclonal antibody; (b) a murine monoclonal antibody; (c) a humanized antibody derived from (b); (d) a human monoclonal antibody; (e) a subhuman primate antibody; and (f) an antibody fragment derived from (a), (b), (c), (d) or (e), in which the antibody fragment may be selected from the group consisting of F(ab')$_2$, F(ab)$_2$, Fab', Fab, Fv, sFv and minimal recognition unit.

The present invention also is directed to a method further comprising the step of (c) administering interferon-γ or interleukin-2 prior to and during the administration of the second vaccine. Alternatively, interleukin-2 and interferon-γ may be given prior to and during the administration of the vaccine.

The present invention also contemplates a method for inducing humoral and cellular immune responses in a mammal against a tumor that expresses a TAA or against a disease caused by an infectious agent, comprising the steps of:
  (a) administering a vaccine to the mammal, wherein the vaccine comprises an antibody component that binds with the TAA or with an antigen associated with the infectious agent, and wherein the antibody component is conjugated with a soluble immunogenic carrier protein; and
  (b) administering an antibody or antigen-binding fragment thereof, wherein the antibody or fragment is not conjugated with a soluble immunogenic carrier protein, and wherein the antibody or fragment binds with the TAA or with an antigen associated with the infectious agent.

The present invention also is directed to such a method in which the antibody or antibody fragment of step (b) is conjugated with biotin, and wherein the method further comprises the step of (c) administering avidin to decrease circulating levels of the biotinylated antibody or the biotinylated antibody fragment.

The present invention also contemplates a method, further comprising the step of (d) administering the vaccine of step (a) a second time.

Moreover, the present invention is directed to a method, further comprising the step of: (e) administering interferon-γ or interleukin-2 prior to and during the second administration of the vaccine. As an alternative, interleukin-2 and interferon-γ may be given prior to and during the administration of the vaccine.

The present invention also contemplates a method for inducing humoral and cellular immune responses in a patient against a tumor that expresses a TAA or against a disease caused by an infectious agent, comprising the steps of:
  (a) obtaining T cells from the patient;
  (b) introducing an expression vector into the T cells to obtain transfected T cells, wherein the expression vector comprises a DNA molecule encoding either a chimeric immunoglobulin/T cell receptor or a chimeric immunoglobulin/CD3 protein, and wherein the immunoglobulin-encoding portion of the DNA molecule encodes the variable region of an antibody that binds with the TAA or with an antigen associated with the infectious agent;
  (c) stimulating the proliferation of the transfected T cells to obtain an increased mass of transfected T cells; and
  (d) returning the increased mass of transfected T cells to the patient.

The present invention also is directed to a method which further comprises the step of: (e) administering a vaccine to the patient, wherein the vaccine comprises an anti-idiotype antibody component that binds with the immunoglobulin moiety of the chimeric immunoglobulin/T cell receptor or the chimeric immunoglobulin/CD3 protein, and wherein the anti-idiotype antibody component is conjugated with a soluble immunogenic carrier protein. As an alternative, at least one cytokine selected from the group consisting of interferon-γ and interleukin-2, may be administered to the patient after returning the transfected T cells and before performing step (e).

The present invention also contemplates a method for inducing humoral and cellular immune responses in a patient against a tumor that expresses a TAA or against a disease caused by an infectious agent, comprising the steps of:
  (a) obtaining T cells from the patient;
  (b) introducing an expression vector into the T cells to obtain transfected T cells, wherein the expression vector comprises a DNA molecule encoding either a chimeric immunoglobulin/T cell receptor or a chimeric immunoglobulin/CD3 protein, and wherein the immunoglobulin-encoding portion of the DNA molecule encodes the variable region of an antibody that mimics an epitope of the TAA or an epitope of an antigen associated with the infectious agent;
  (c) stimulating the proliferation of the transfected T cells to obtain an increased mass of transfected T cells; and
  (d) returning the increased mass of transfected T cells to the patient.

Moreover, the present invention contemplates a method which further comprises the step of: (e) administering a vaccine to the patient, wherein the vaccine comprises an antibody component that binds with the immunoglobulin moiety of the chimeric immunoglobulin/T cell receptor or the chimeric immunoglobulin/CD3 protein, and wherein the antibody component is conjugated with a soluble immunogenic carrier protein. As an alternative, at least one cytokine selected from the group consisting of interferon-γ and interleukin-2, may be administered to the patient after returning the transfected T cells and before performing step (e).

The present invention also is directed to a vaccine for treating a patient having a tumor that expresses carcinoembryonic antigen (CEA), comprising a pharmaceutically acceptable carrier and therapeutically effective amount of an anti-CEA antibody component which is conjugated with a soluble immunogenic carrier protein. The anti-CEA antibody component may be selected from the group consisting of: (a) a murine monoclonal Class III anti-CEA antibody; (b) a humanized antibody derived from a murine monoclonal Class III anti-CEA antibody; (c) a human monoclonal anti-CEA antibody; and (d) an antibody fragment derived from (a), (b) or (c).

The present invention also contemplates a vaccine for treating a patient having a tumor that expresses CEA, comprising a pharmaceutically acceptable carrier and therapeutically effective amount of ah anti-idiotype antibody component which is conjugated with a soluble immunogenic carrier protein, wherein the anti-idiotype antibody component mimics an epitope of CEA. The anti-idiotype antibody component may be selected from the group consisting of: (a) a polyclonal antibody that binds with the variable region of a Class III anti-CEA antibody; (b) a monoclonal antibody that binds with the variable region of a Class III anti-CEA antibody; (c) a humanized antibody derived from (b); (d) a subhuman primate antibody that binds with the variable region of a Class III anti-CEA antibody; (e) a human monoclonal anti-CEA antibody that binds with the variable region of a Class III anti-CEA antibody; and (f) an antibody fragment derived from (a), (b), (c), (d) or (e).

The present invention also contemplates a method for inducing humoral and cellular immune responses in a mammal against a tumor that expresses a TAA or against a disease caused by an infectious agent, comprising the steps of:

(a) administering a first vaccine to the mammal, wherein the first vaccine comprises an antibody that binds with the TAA or with an antigen associated with the infectious agent, and wherein the antibody component is conjugated with a soluble immunogenic carrier protein;

(b) administering an antibody or antigen-binding fragment thereof, wherein the antibody or fragment is not conjugated with a soluble immunogenic carrier protein, and wherein the antibody or fragment binds with the TAA or with an antigen associated with the infectious agent; and (c) administering a second vaccine to the mammal, wherein the second vaccine comprises an anti-idiotype antibody that mimics an epitope of the TAA or the infectious agent antigen, and wherein the anti-idiotype antibody component is conjugated with a soluble immunogenic carrier protein.

Preferably, such a method is performed wherein the first vaccine comprises a Class III anti-CEA antibody, wherein the antibody of step (b) is a Class III anti-CEA antibody, and wherein the second vaccine comprises an antibody that binds with the variable region of a Class III anti-CEA antibody.

The present invention also is directed to a method for treating a patient having a tumor that expresses CEA, comprising the step of administering bispecific antibody to the patient, wherein the bispecific antibody comprises a moiety that binds with CD3 protein and a moiety that binds with CEA, and wherein the CEA-binding moiety is derived from a Class III anti-CEA antibody.

DETAILED DESCRIPTION

1. Definitions

In the description that follows, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

An isolated DNA molecule is a fragment of DNA that is not integrated in the genomic DNA of an organism. For example, a cloned T cell receptor gene is a DNA fragment that has been separated from the genomic DNA of a mammalian cell. Another example of an isolated DNA molecule is a chemically-synthesized DNA molecule that is not integrated in the genomic DNA of an organism.

An enhancer is a DNA regulatory element that can increase the efficiency of transcription, regardless of the distance or orientation of the enhancer relative to the start site of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary. DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A tumor associated antigen is a protein normally not expressed, or expressed at very low levels, by a normal counterpart. Examples of tumor associated antigens include α-fetoprotein and carcinoembryonic antigen (CEA).

As used herein, an infectious agent denotes both microbes and parasites. A "microbe" includes viruses, bacteria, rickettsia, mycoplasma, protozoa, fungi and like microorganisms. A "parasite" denotes infectious, generally microscopic or very small multicellular invertebrates, or ova or juvenile forms thereof, which are susceptible to antibody-induced clearance or lytic or phagocytic destruction, such as malarial parasites, spirochetes, and the like.

In the present context, an anti-CEA MAb is a Class III MAb, as described by Primus et al., *Cancer Research* 43: 686 (1983) and by Primus et al., U.S. Pat. No. 4,818,709, which are incorporated by reference.

As used herein, an Ab1 is an antibody that binds with a tumor associated antigen or an antigen associated with an infectious agent.

An anti-idiotype antibody (Ab2), as used herein, is an antibody that binds with an Ab1. Importantly, an Ab2 binds with the variable region of Ab1 and thus, an Ab2 mimics an epitope of a tumor associated antigen or an epitope of an infectious agent associated antigen.

An antibody fragment is a portion of an antibody such as F(ab')$_2$, F(ab)$_2$, Fab', Fab, and the like. Regardless of structure, an antibody fragment binds with the same antigen that is recognized by the intact antibody. For example, an anti-CEA Mab (Ab1) fragment binds with CEA, while an Ab2 fragment binds with the variable region of the Ab1 and mimics an epitope of CEA.

The term "antibody fragment" also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

Humanized antibodies are recombinant proteins in which murine complementarity determining regions of MAb have been transferred from heavy and light variable chains of the murine immunoglobulin into a human variable domain.

As used herein, the term antibody component includes both an entire antibody and an antibody fragment.

In the present context, a chimeric immunoglobulin/T cell receptor is a functional T cell receptor in which the variable regions of a and B polypeptide chains have been replaced by variable segments of the heavy and light chain of either an antibody (Ab1) or an anti-idiotype antibody (Ab2).

As used herein, a chimeric immunoglobulin/CD3 protein is a recombinant protein that retains the function of a CD3 polypeptide and comprises variable segments of the heavy and light chain of either an Ab1 or an Ab2.

2. Production of Monoclonal Antibodies, Humanized Antibodies, Primat Antibodies and Human Antibodies Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1–2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

A wide variety of monoclonal antibodies against tumor associated antigens or infectious agents have been developed. See, for example, Goldenberg et al. international application publication No. WO 91/11465 (1991), and Goldenberg, international application publication No. WO 94/04702 (1994), each of which is incorporated by reference in its entirety.

An example of a suitable Mab is a Class III anti-CEA Mab. Conventional antisera raised against CEA usually contain antibodies that react with a group of substances closely related to CEA. The major members of this family of CEA-related antigens are (1) the normal cross-reactive antigen (NCA), which shares a similar tissue distribution with CEA, and (2) meconium antigen (MA), which shares almost identical physiochemical properties with CEA. The first panel of monoclonal antibodies (MAb) that defined NCA-cross-reactive, MA-cross-reactive, and CEA-specific epitopes on the CEA molecule were described by Primus et al., *Cancer Research* 43: 686 (1983). In particular, three classes of anti-CEA antibody were identified: 1) Class I antibodies, which react with CEA, NCA and MA; 2) Class II antibodies, which react with CEA and MA, but not with NCA; and 3) Class III antibodies, which are specific for CEA and do not bind with NCA or MA. Methods for obtaining Class III anti-CEA MAbs are disclosed by Primus et al., *Cancer Research* 43: 686 (1983), and Primus et al., U.S. Pat. No. 4,818,709. Moreover, the production of second generation Class III anti-CEA MAbs is disclosed by Hansen et al., *Cancer* 71: 3478 (1993), and U.S. Pat. No. 5,874,540, which are incorporated by reference.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in METHODS IN MOLECULAR BIOLOGY, VOL. 10, pages 79–104 (The Humana Press, Inc. 1992).

In another embodiment, an antibody of the present invention is a subhuman primate antibody. General techniques for raising therapeutically useful antibodies in baboons may be found, for example, in Goldenberg et al., international patent publication No. WO 91/11465 (1991), and in Losman et al., *Int. J. Cancer* 46: 310 (1990), which is incorporated by reference.

In yet another embodiment, an antibody of the present invention is a "humanized" monoclonal antibody. That is, mouse complementarity determining regions are transferred from heavy and light variable chains of the mouse immunoglobulin into a human variable domain, followed by the replacement of some human residues in the framework regions of their murine counterparts. Humanized monoclonal antibodies in accordance with this invention are suitable for use in therapeutic methods. General techniques for cloning murine immunoglobulin variable domains are described, for example, by the publication of (1989), which is incorporated by reference in its entirety. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

In another embodiment, an antibody of the present invention is a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7: 13 (1994), Lonberg et al., *Nature* 368: 856 (1994), and Taylor et al., *Int. Immun.* 6: 579 (1994), which are incorporated by reference.

3. Production of Antibody Fragments

The present invention contemplates the use of fragments of Ab1 or Ab2. Antibody fragments can be prepared by proteolytic hydrolysis of the antibody or by expression in *E. coli* of the DNA coding for the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')₂. This fragment can be further cleaved using a thiol reducing agent, and optionally a blocking group for th sulfhydryl groups resulting from cleavage of disulfide linkages, to produce 3.5S Fab' monovalent fragments. Alternatively, an enzymatic cleavage using pepsin produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, Biochem. J. 73: 119 (1959), Edelman et al., in *METHODS IN ENZYMOLOGY VOL.* 1, page 422 (Academic Press 1967), and Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described in Inbar et al., *Proc. Nat'l Acad. Sci. USA* 69: 2659 (1972). Alternatively, the variable chains can be linked by an intermolecular disulfide bond or cross-linked by chemicals such as glutaraldehyde. See, for example, Sandhu, supra.

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2: 97 (1991). Also see Bird et al., *Science* 242:423–426 (1988), Ladner et al., U.S. Pat. No. 4,946,778, Pack et al., *Bio/Technology* 11:1271–1277 (1993), and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991).

4. Production of Anti-Idiotype Antibodies (Ab2)

Polyclonal Ab2 can be prepared by immunizing animals with Ab1 or fragments, using standard techniques. See, for example, Green et al., "Production of Polyclonal Antisera," in METHODS IN MOLECULAR BIOLOGY: IMMUNOCHEMICAL PROTOCOLS, Manson (ed.), pages 1–12 (Humana Press 1992). Also, see Coligan at pages 2.4.1–2.4.7.

Alternatively, monoclonal Ab2 can be prepared using Ab1 or fragments as immunogens with the techniques, described above. The preparation of a rat monoclonal Ab2 is illustrated in Example 3.

As another alternative, humanized Ab2 or subhuman primate Ab2 can be prepared using the above-described techniques.

5. Production of Bispecific Antibodies

Bispecific antibodies can be used to recruit and target T cells to a tumor cell. A bispecific antibody is a hybrid molecule that consists of nonidentical light and heavy chain pairs, providing two distinct antibody specificities. For example, bispecific antibodies have been produced with one binding site recognizing the CD3 signal transducing protein on T cells and a second binding site for a tumor-associated antigen. See, for example, Canevari et al., *Int. J. Cancer* 42: 18 (1988); Lanzaveccia et al., *Eur. J. Immunl.* 17: 105 (1987); Van Dijk et al., *Int. J. Cancer* 43: 344 (1989); and Renner et al., *Science* 264: 833 (1994).

Bispecific antibodies can be made by a variety of conventional methods, e.g., disulfide cleavage and reformation of mixtures of whole antibody or, preferably F(ab')₂ fragments, fusions of more than one hybridoma to form polyomas that produce antibodies having more than one specificity, and by genetic engineering. Bispecific antibodies have been prepared by oxidative cleavage of Fab' fragments resulting from reductive cleavage of different antibodies. See, for example, Winter et al., *Nature* 349: 293 (1991). This is advantageously carried out by mixing two different F(ab')₂ fragments produced by pepsin digestion of two different antibodies, reductive cleavage to form a mixture of Fab' fragments, followed by oxidative reformation of the disulfide linkages to produce a mixture of F(ab')₂ fragments including bispecific antibodies containing a Fab' portion specific to each of the original epitopes. General techniques for the preparation of such antibody composites may be found, for example, in Nisonhoff et al., *Arch Biochem. Biophys.* 93: 470 (1961), Hammerling et al., *J. Exp. Med.* 128: 1461 (i968), and U.S. Pat. No. 4,331,647.

More selective linkage can be achieved by using a heterobifunctional linker such as maleimide-hydroxysuccinimide ester. Reaction of the ester with an antibody or fragment will derivatize amine groups on the antibody or fragment, and the derivative can then be reacted with, e.g., an antibody Fab fragment having free sulfhydryl groups (or, a larger fragment or intact antibody with sulfhydryl groups appended thereto by, e.g., Traut's Reagent). Such a linker is less likely to crosslink groups in the same antibody and improves the selectivity of the linkage.

It is advantageous to link the antibodies or fragments at sites remote from the antigen binding sites. This can be accomplished by, e.g., linkage to cleaved interchain sulfydryl groups, as noted above. Another method involves reacting an antibody having an oxidized carbohydrate portion with another antibody which has at lease one free amine function. This results in an initial Schiff base (imine) linkage, which is preferably stabilized by reduction to a secondary amine, e.g., by borohydride reduction, to form the final composite. Such site-specific linkages are disclosed, for small molecules, in U.S. Pat. No. 4,671,958, and for larger addends in U.S. Pat. No. 4,699,784.

In the present context, a bispecific antibody comprises binding moieties for T cells and an antigen that is associated with a tumor cell or infectious agent. For example, a CEA binding moiety can be derived from a Class III Mab and the T cell-binding moiety can be derived from anti-CD3 Mab. Methods for preparing anti-CD 3 antibodies are well-known to those of skill in the art. See, for example, Canevari et al., supra, Van Dijk et al., supra, Hansen et al., "Human T Lymphocyte Cell Surface Molecules Defined by the Workshop Monoclonal Antibodies (T Cell Protocol)," in LEUKOCYTE TYPING: HUMAN LEUKOCYTE MARKERS DETECTED BY MONOCLONAL ANTIBODIES, Bernard et al., (eds.) pages 195–212 (Springer-Verlag 1984); and U.S. Pat. No. 4,361,549. Alternatively, anti-CD3 antibodies can be obtained from commercial sources such as Boehringer Mannheim Corp. (Indianapolis, Ind.; Cat. No. 1273 485) and the American Type Culture Collection (Rockville, Md.; ATCC CRL 8001 [OKT-3]).

For example, a bispecific antibody can be prepared by obtaining an F(ab')$_2$ fragment from an anti-CEA Class III Mab, as described above. The interchain disulfide bridges of the anti-CEA Class III F(ab')$_2$ fragment are gently reduced with cysteine, taking care to avoid light-heavy chain linkage, to form Fab'-SH fragments. The SH group(s) is(are) activated with an excess of bis-maleimide linker (1,1'-(methylenedi-4,1-phenylene)bis-malemide). The anti-CD3 Mab is converted to Fab'-SH and then reacted with the activated anti-CEA Class III Fab'-SH fragment to obtain a bispecific antibody.

Alternatively, such bispecific antibodies can be produced by fusing two hybridoma cell lines that produce anti-CD3 Mab and anti-CEA Class III Mab. Techniques for producing tetradomas are described, for example, by Milstein et al., *Nature* 305: 537 (1983) and Pohl et al., *Int. J. Cancer* 54: 418 (1993).

Finally, bispecific antibodies can be produced by genetic engineering. For example, plasmids containing DNA coding for variable domains of an anti-CEA Class III Mab can be introduced into hybridomas that secrete anti-CD 3 antibodies. The resulting "transfectomas" produce bispecific antibodies that bind CEA and CD3. Alternatively, chimeric genes can be designed that encode both anti-CD3 and anti-CEA binding domains. General techniques for producing bispecific antibodies by genetic engineering are described, for example, by Songsivilai et al., *Biochem. Biophys. Res. Commun.* 164: 271 (1989); Traunecker et al., *EMBO J.* 10: 3655 (1991); and Weiner et al., *J. Immunol.* 147: 4035 (1991).

6. The Use of Antibodies and Cytokines to Amplify the Humoral and Cellular Immune Response Against Tumor Cells and Infectious Agents The present invention contemplates the therapeutic use of Ab1, Ab2 generated against Ab1, and fragments of either Ab1 or Ab2. These antibodies and fragments can be used as vaccines to induce both humoral and cellular immune responses in the recipient mammal. Moreover, the administration of Ab1 and/or bispecific antibodies can be used to amplify the integrated immune response.

According to one method of the present invention, a mammal is immunized with a vaccine comprising Ab1 or fragments thereof, to induce the production of Ab2 and T cells (T2 cells). After the mammal begins to produce T2 cells, the mammal may be given Ab1, or fragments thereof, by intravenous administration to expand the T2 cell mass. An additional advantage of this second administration is that the antibodies or fragments bind with cognate antigen on cancer cells or infectious organisms and thus, serve as targets for T2 cells. Methods for detecting the production of T cells that react with specific antibodies are well-known to those of ordinary skill in the art. See, for example, Fagerberg et al., *Cancer Immunol. Immunother.* 37: 264 (1993), which is incorporated by reference.

According to a preferred method, a mammal is subsequently immunized with a vaccine comprising Ab2, or fragments thereof, to induce the formation of Ab3 and T cells that recognize Ab2 (T3 cells). An advantage of this subsequent Ab2 vaccination is that cells expressing a tumor associated antigen or infectious agent antigen are destroyed by T3 cells directed to the antigen, and by T2 cells directed to Ab3, which also is bound by the antigen. Example 4 illustrates a method of treatment comprising the administration of an Ab1 vaccine, Ab1 (or fragments), and an Ab2 vaccine.

In addition, the T2 response may be further amplified by the intravenous administration of Ab1 antibodies or fragments after Ab2 vaccination.

It is possible that the efficacy of the Ab2 vaccine may be decreased by the presence of circulating Ab1 antibodies, which have been administered intravenously. Therefore, it is advantageous to clear circulating Ab1 prior to the administration of Ab2 vaccine. One method that can be used to achieve Ab1 clearance is to use Ab1 antibodies that have been conjugated with biotin. In this way, circulating biotinylated Ab1 can be cleared prior to Ab2 vaccination by the intravenous administration of avidin. Preferably, clearance with avidin is performed one to two days after the intravenous administration of Ab1 (or fragments thereof). This antibody clearance technique is described by Goldenberg, international application publication No. WO 94/04702 (1994).

In an alternative method of immunotherapy, a mammal is immunized with an Ab1 vaccine, treated with Ab1 (or fragments) to saturate a high percentage of tumor or infectious agent antigen sites and then, hyperimmunized with Ab1 vaccine to generate large numbers of cytotoxic lymphocytes directed against cells coated with Ab1 (or fragments thereof).

According to preferred methods of immunotherapy, the immune response is further amplified by the administration of cytokines. Examples of cytokines include the interferons (INFs), interleukins (ILs) and tumor necrosis factors. INF-$\gamma$ induces macrophages, as well as cell-surface class II histocompatibility antigens on lymphoid cells and monocytes. See, for example, Klegerman et al., "Lymphokines and Monokines," in BIOTECHNOLOGY AND PHARMACY, Pezzuto et al. (eds.), pages 53–70 (Chapman & Hall 1993), and Roitt et al., IMMUNOLOGY, 3rd Edition, pages 7.8–7.14. (Mosby 1993). IL-2 is a T cell growth factor and a stimulator of natural killer cells and tumor-reactive T cells. Id. Thus, INF-$\gamma$ and IL-2 are preferred cytokines for the augmentation of the immune response.

The antibodies and fragments of the present invention can be used as vaccines by conjugating the antibodies or fragments to a soluble immunogenic carrier protein. Suitable carrier proteins include keyhole lympet hemocyanin, which is the preferred carrier protein. The antibodies and fragments can be conjugated to the carrier protein using standard methods. See, for example, Hancock et al, "Synthesis of Peptides for Use as Immunogens," in METHODS IN MOLECULAR BIOLOGY: IMMUNOCHEMICAL PROTOCOLS, Manson (ed.), pages 23–32 (Humana Press 1992).

A preferred vaccination composition comprises an antibody conjugate or fragment conjugate, and an adjuvant. Examples of suitable adjuvants include aluminum hydroxide and lipid. Methods of formulating vaccine compositions are well-known to those of ordinary skill in the art. See, for example, Rola, "Immunizing Agents and Diagnostic Skin Antigens," in REMINGTON'S PHARMACEUTICAL SCIENCES, 18th Edition, Gennaro (ed.), pages 1389–1404 (Mack Publishing Company 1990).

Additional pharmaceutical methods may be employed to control the duration of action of a vaccine in a therapeutic application. Control release preparations can be prepared through the use of polymers to complex or adsorb the antibodies or fragments. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an antibody or antibody fragment from such a matrix depends upon the molecular weight of the antibody or fragment, the amount of antibody or fragment within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990).

The antibody preparations of the present invention can be formulated according to known methods to prepare pharmaceutically useful compositions, whereby antibodies or antibody fragments are combined in a mixture with a pharmaceutically acceptable carrier. A composition is said to be a "pharmaceutically acceptable carrier" if its administration can be tolerated by a recipient mammal. Sterile phosphate-buffered saline is one example of a pharmaceutically acceptable carrier. Other suitable carriers are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990).

The antibodies or fragments may be administered to a mammal intravenously or subcutaneously. Moreover, the administration may be by continuous infusion or by single or multiple boluses. Preferably, an antibody vaccine is administered subcutaneously, while an antibody preparation that is not a vaccine is administered intravenously. In general, the dosage of administered antibodies or fragments for humans will vary depending upon such factors as the patient's age, weight, height, sex, general medical condition and previous medical history. Typically, it is desirable to provide the recipient with a dosage of antibodies or fragments which is in the range of from about 1 pg/kg to 10 mg/kg (amount of agent/body weight of patient), although a lower or higher dosage also may be administered as circumstances dictate.

For purposes of therapy, antibodies or fragments are administered to a mammal in a therapeutically effective amount. An antibody preparation is said to be administered in a "therapeutically effective amount" if the amount administered is physiologically significant. An agent is physiologically significant if its presence results in a detectable change in the physiology of a recipient mammal. In particular, an antibody preparation of the present invention is physiologically significant if its presence invokes a humoral and/or cellular immune response in the recipient mammal.

A cytokine, such as INF-γ or IL-2, may be administered before and during the administration of an Ab1 vaccine or an Ab2 vaccine. Alternatively, INF-γ and IL-2, may be administered together before and during the administration of an antibody vaccine. Cytokines are administered to the mammal intravenously, intramuscularly or subcutaneously. For example, recombinant IL-2 may be administered intravenously as a bolus at $6 \times 10^5$ IU/kg or as a continuous infusion at a dose of $18 \times 10^6$ IU/m²/d. Weiss et al., *J. Clin. Oncol.* 10: 275 (1992). Alternatively, recombinant IL-2 may be administered subcutaneously at a dose of $12 \times 10^6$ IU. Vogelzang et al., *J. Clin. Oncol.* 11: 1809 (1993). Moreover, INF-γ may be administered subcutaneously at a dose of $1.5 \times 10^6$ U. Lienard et al., *J. Clin. Oncol.* 10: 52 (1992). Suitable IL-2 formulations include PROLEUKIN (Chiron Corp./Cetus Oncology Corp.; Emeryville, —CA) and TECELEUKIN (Hoffman-La Roche, Inc.; Nutley, N.J.), while ACTIMMUNE (Genentech, Inc.; South San Francisco, Calif.) is a suitable INF-γ preparation.

In addition, bispecific antibodies may be administered after the initial Ab1 treatment. The function of the bispecific antibodies is to bridge lymphocytes with CEA-bearing tumor cells and to trigger the lymphocyte-mediated cytolysis. Bispecific antibodies can be administered according to above-described general guidelines. However, bispecific antibodies, unlike antibody vaccines, are not conjugated with immunogens.

Those of ordinary skill in the art will appreciate that the above-described methods can be used to provide prophylaxis against infectious agents. Thus, the present invention contemplates the use of methods described herein to provide protection to a mammal before exposure to an infectious agent.

7. The Production and Therapeutic Use of T Cells that Express Chimeric Immunoglobulin/T Cell Receptors or Chimeric Immunoglobulin/CD3 Proteins T cells can be divided into two mutually exclusive populations: T cells that express α and β T cell receptor (TCR) polypeptides, and T cells that express γ and δ TCR polypeptides. See, generally, Roitt et al., *IMMUNOLOGY*, 3rd Edition (Mosby 1993), and Bolhuis et al., *Cancer Immunol. Immunother.* 34: 1 (1991). The αβ polypeptide set is expressed by more than 95% of peripheral T cells and the vast majority of TCR-expressing thymocytes. In contrast, the γδ polypeptide set is expressed by a minor proportion of T cells in the thymus and secondary lymphatic organs, while the δδ T cells are abundant in various epithelia.

Each polypeptide chain of a TCR heterodimer comprises two external variable and constant immunoglobulin-like domains that are anchored into the plasma membrane by a transmembrane peptide and a short cytoplasmic tail. The N-terminal domains of the TCR polypeptides contain variable regions that are homologous with the variable domains of immunoglobulins. Moreover, analysis of these TCR variable domains has revealed areas of relatively greater variability which correspond to immunoglobulin hypervariable regions (CDRs). The variable domains of the αβ and γδ polypeptides are thought to associate in a manner that is similar to the association of $V_H/V_L$ domains of immunoglobulin molecules, bringing six TCR hypervariable regions together to form an antigen binding site.

The TCR αβ and γδ polypeptides are both noncovalently associated with a series of polypeptides (γ, δ, ε, ζ, and η) collectively designated CD3 to form the complete TCR complex. In contrast to the TCR polypeptides, the amino acid sequences of CD3 components show no variability on different T cells and thus, the CD3-components cannot generate the diversity associated with TCR polypeptides. Instead, the CD3 component of the TCR complex is required for the transduction of signals generated by TCR-antigen interaction.

In general, T cells recognize cell-bound antigen in association with major histocompatibility complex (MHC) molecules on the surface of the antigen-presenting cell. However, methods are available to produce T cells that are targeted to particular tumors and that are not MHC-restricted. Bispecific antibodies, described above, provide one approach to targeting T cells. Another approach is to genetically engineer T cells having chimeric immunoglobulin/T cell receptors. To be effective, the chimeric immunoglobulin/TCRs must be expressed by T cells in a stable manner, and the chimeric immunoglobulin/TCRs must form a functional association with CD3 signal-transducing polypeptides.

Functional chimeric immunoglobulin/TCRs have been produced in which the variable gene segments of the TCR α and β chains were replaced by variable gene-segments of the heavy and light chain of an immunoglobulin. See, for example, Becker et al., *Cell* 58: 911 (1989), Eshhar et al., *Br. J. Cancer* 62 (Suppl. 10): 27 (1990), Goverman et al., *Cell* 60: 929 (1990), Gross et al., *Transplant Proc.* 21: 127 (1989a), and Gross et al., *Proc. Nat'l Acad. Sci. USA* 86: 10024 (1989b), which are incorporated by reference. The present invention contemplates construction of chimeric immunoglobulin/TCRs in which variable regions of the TCR α and β chains are replaced by variable gene segments of the heavy and light chain of either an Ab1 or an Ab2.

In addition, functional chimeric immunoglobulin/CD3 proteins have been produced in which DNA fragments encoding immunoglobulin variable segments were fused with DNA fragments encoding γ, ζ or η CD3 polypeptides. See, for example, Seed et al., international application publication No. WO 92/15322 (1992), and Eshhar et al., *Proc. Nat'l Acad. Sci. USA* 90: 720 (1993), which are incorporated by reference. Thus, the present invention also contemplates the construction of chimeric immunoglobulin/CD3 proteins comprising variable gene segments of the heavy and light chain of either an Ab1 or an Ab2.

Chimeric immunoglobulin/TCRs and chimeric immunoglobulin/CD3 proteins can be constructed using standard techniques. Typical techniques are illustrated by the following methods that can be used to construct an anti-CEA (or Ab2)/TCR.

DNA molecules encoding the variable regions of anti-CEA Mab or anti-idiotype Mab can be synthesized using the polymerase chain reaction with RNA from hybridomas that produce such antibodies. General techniques for the synthesis of murine variable regions and suitable primers are described, for example, by Orlandi et al., supra, Larrick et al., *Methods: A Companion to Methods in Enzymology* 2: 106 (1991), and by Kang et al., *Id.* at 111.

Methods for obtaining DNA molecules encoding human T cell receptor polypeptides are well-known to those of ordinary skill in the art. See, for example, Bougueleret et al., *Immunogenetics* 26: 304 (1987), and Luria et al., *EMBO J.* 6: 3307 (1987). Moreover, techniques for constructing chimeric immunoglobulin/TCRs and inserting the chimeric genes into expression vectors have been described, for example, by Becker et al., supra, Eshhar et al., supra, Goverman et al., supra, Gross et al. (1989a), supra, and Gross et al. (1989b), supra. Furthermore, standard protocols for constructing immunoglobulin fusion proteins are described by Coligan at pages 10.19.1–10.19.11. Preferred expression vectors contain a dominant selectable marker for the production of stably-transfected cells.

Expression vectors comprising chimeric immunoglobulin/TCR genes are introduced into human T cells. Human peripheral blood cells can be obtained by simple venipuncture and fractionated by Ficoll-Hypaque gradient separation to obtain a mononuclear cell fraction. See, for example, Coligan at pages 7.1.1–7.1.2. T cells are then separated from other mononuclear cells using a rosetting procedure. *Id.* at pages 7.2.1–7.2.4. Expression vectors are introduced into the human T cell fraction by electroporation or other well-known techniques. See, for example, Co et al., *J. Immunol.* 148: 1149 (1992), and Coligan at pages 10.13.2–10.17.7.

Alternatively, chimeric immunoglobulin/TCRs can be introduced into T cells by retrovirus-mediated gene transfer. An advantage of this approach is that all proviral copies become stably integrated into the chromosomes of the T cells and this ensures constitutive expression of chimeric immunoglobulin/TCRs. Methods for transfecting human T cells by retrovirus-mediated gene transfer are described by Kasid et al., *Proc. Nat'l Acad. Sci. USA* 87: 473 (1990), Rosenberg et al., *N. Engl. J. Med.* 323: 570 (1990), and Morecki et al., *Cancer Immunol. Immunother.* 32: 342 (1991).

Transfected cells that carry the expression vector are selected using a dominant selectable marker. For example, G418 can be used to select transfected T cells carrying an expression vector having the aminoglycoside phosphotransferase gene. Southern et al., *J. Mol. Appl. Gen.* 1: 327 (1982). A method for G4.18 selection of transfected human T cells is described by Morecki et al., supra. Alternatively, hygromycin-B can be used to select transfected cells carrying an expression vector having the hygromycin-B-phosphotransferase gene. Palmer et al., *Proc. Nat'l Acad. Sci. USA* 84: 1055 (1987). Moreover, aminopterin and mycophenolic acid can be used to select transfected cells carrying an expression vector having the xanthine-guanine phosphoribosyltransferase gene. Mulligan et al., *Proc. Nat'l. Acad. Sci. USA* 78: 2072 (1981).

Stably transfected T cells must be expanded in culture before the cells are administered to a patient. The proliferation of T cells can be induced by incubating the cells with the appropriate antigen. For example, a purified preparation of CEA can be used to induce proliferation of T cells expressing chimeric anti-CEA/TCR polypeptides, whereas a purified preparation of anti-CEA antibody (or fragments thereof) can be used to stimulate T cells expressing the chimeric anti-idiotype/TCR polypeptides. A standard technique for antigen-induced T cell proliferation is described by Coligan at page 7.10.4. In the present context, another important function of antigen-induced T cell proliferation is the verification of the presence of functional immunoglobulin/TCR or functional immunoglobulin/CD3 protein.

After culture expansion, the T cells are returned to the patient by intravenous infusion or by intraperitoneal administration. See, for example, Rosenberg et al., *Science* 233: 1318 (1986), Rosenberg et al., *N. Engl. J. Med.* 319: 1676 (1988), Hercend et al., *J. Biol. Response Modif.* 9: 546 (1990), Rosenberg et al., *N. Engl. J. Med.* 323: 570 (1990), and Bartholeyns et al., *Anticancer Res.* 11: 1201 (1991).

In summary, genetic engineering can be used to produce transformed human T cells that express chimeric immunoglobulin/TCRs or chimeric immunoglobulin/CD3 proteins. T cells that express Ab1/TCRs or Ab1/CD3 proteins correspond to T3 cells, while T cells expressing anti-idiotype (Ab2)/TCRs or Ab2/CD3 proteins correspond to T2 cells.

Several methods can be used to enhance the efficacy of adoptive immunotherapy. After administration of T cells that express Ab1/TCRs or Ab1/CD3 proteins, an Ab2 vaccine may be administered to expand the infused T cells in vivo. Similarly, the administration of T cells that express Ab2/TCRs or Ab2/CD3 proteins may be followed by Ab1 vaccination. In either case, the immune response may be amplified further by administering INF-γ, IL-2, or INF-γ and IL-2 after the administration of transformed T cells. Thus, antibody vaccination and cytokine treatment can be used to complement and augment the efficacy of adoptive immunotherapy with transformed T cells.

The present invention, thus generally described, will be understood more readily by reference to the following examples, which are provided by way of illustration and are not intended to be limiting of the present invention.

EXAMPLE 1

Production of Murine Anti-CEA MAb (MN-14)

The production of MN-14, a Class III, anti-CEA MAb, has been described by Hansen et al., *Cancer* 71: 3478 (1993), which is incorporated by reference, and in U.S. Pat. No. 5,874,540. Briefly, a 20 gram BALB/c female mouse was immunized subcutaneously with 7.5 µg of partially-purified CEA in complete Freund adjuvant. On day 3, the mouse was boosted subcutaneously with 7.5 µg of CEA in incomplete Freund adjuvant and then, the mouse was boosted intravenously with 7.5 µg of CEA in saline on days 6 and 9. On day 278, the mouse was given 65 µg of CEA intravenously in saline and 90 µg of CEA in saline on day 404. On day 407, the mouse was sacrificed, a cell suspension of the spleen was prepared, the spleen cells were fused with murine myeloma cells, SP2/0-Ag 14 (ATCC CRL 1581) using polyethylene glycol, and the cells were cultured in medium containing 8-azaguanine. Hybridoma supernatants were screened for CEA-reactive antibody using an $^{125}$I-CEA radioimmunoassay (Roche; Nutley, N.J.). Positive clones were recloned.

One clone, designated MN-14, had properties similar to the Class III anti-CEA-specific MAb, NP-4, being unreactive with normal cross-reactive antigen and meconium antigen. However, MN-14, compared with NP-4, demonstrated significantly superior tumor targeting in a human colon tumor xenograft model and consistently stronger staining of frozen sections of colon cancer.

EXAMPLE 2

Preparation of CDR-Grafted MN-14 (hMN-14) and hAb1 Vaccine (hMN-14 Vaccine)

A modified antibody was prepared in which the complementarity determining regions (CDR) of MN-14 were engrafted to the framework regions of human IgG$_1$ antibody. The CDR-grafted ("humanized") MN-14 antibody was designated "hMN-14." General techniques for producing humanized antibodies are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Biotech.* 12: 437 (1992), and Singer et al., *J. Immun.* 150: 2844 (1993).

To prepare hMN-14 vaccine, hMN-14 was conjugated with keyhole lympet hemocyanin. Typically, patients are immunized with subcutaneous injections of the conjugate (2 mg/injection) mixed with 100 µl (10$^7$ organisms) of Tice *Bacillus Calmette-Guérin* (Organon; West Orange, N.J.)

EXAMPLE 3

Preparation of Rat Monoclonal Ab2 to MN-14 (WI2) and Ab2 Vaccine (WI2 Vaccine)

Rat Ab2 to MN-14 was prepared as described by Losman et al., *Int. J. Cancer* 56: 580 (1994), which is incorporated by reference. Briefly, female 3-week-old Copenhagen rats were injected-intraperitoneally with 200 µg of MN-14 F(ab')$_2$ fragments emulsified in Freund's complete adjuvant. Animals were boosted at days 200, 230, and 235 with the same amount of antigen in Freund's incomplete adjuvant. Four days after the last injection, animals were sacrificed, spleen cell suspensions were prepared, and the cells were fused with murine non-secreting plasmocytoma SP2/0 using standard techniques. Hybridoma cells were cultured in the presence of rat peritoneal feeder cells (10,000 cells/200 µl culture well).

Culture supernatants were screened by ELISA for reactivity with MN-14 and absence of reactivity with control murine MAbs. Positive hybridomas were cloned at least twice by limiting dilution in the presence of rat peritoneal feeder cells.

WI2 is an IgG$_1$, Ab2 which is specific for MN-14 and does not react with other isotype-matched anti-CEA MABs. Immunization of mice or rabbits with WI2 (but not with control rat IgG) induced the production of Ab1' anti-CEA antibodies. Thus, WI2 can be used as an idiotype vaccine for patients with CEA-producing tumors.

WI2 vaccine is prepared from WI2 as described for the preparation of hMN-14 vaccine.

EXAMPLE 4

Treatment with hMN-14 Vaccine (hAb1-Vaccine) and W12 Vaccine (Ab2 Vaccine)

A patient with Dukes C colon carcinoma underwent a primary tumor resection for cure and then, was placed on fluorouracil and Levamisole adjuvant therapy. The pre-operative CEA titer was 15.5 ng/ml. Three months after primary surgery, the CEA titer was in the normal range, that is, below 2.5 ng/ml.

Two years later, the patient was found to have a CEA titer of 25 ng/ml and a CAT scan showed a 5 cm tumor in the left lobe of liver and a 2 cm tumor in the right lobe. One month later, the CEA titer was 25 ng/ml and the patient was immunized subcutaneously with 2 mg of hAb1 vaccine (day 0). Immunization was repeated at day 7.

On day 30, the patient was found to have lymphocytes reactive with the Ab1 (T2 cells). On day 40, the patient was given 100 mg of the hAb1 intravenously. Two months later, the CEA titer was 5 ng/ml and a CAT scan showed that the left lobe tumor had decreased to 2 cm in size, while the right lobe tumor had completely regressed.

Six months later, the left lobe tumor had increased in size, and a large tumor mass was found in the abdomen, as confirmed by needle biopsy. The CEA titer had increased to 50 ng/ml. The patient was given the WI2 Ab2 vaccine (2 mg) subcutaneously on day 0 and on day 30. A severe reaction occurred at the injection site on day 35, which slowly resolved.

Three months later, the CEA titer was found to be less than 2.5 ng/ml, and the left lobe tumor had completely resolved. The mass in the abdomen was reduced in size and a needle biopsy failed to reveal the presence of a tumor, demonstrating only fibrous tissue infiltrated with lymphocytes.

Two years later, a CAT scan showed that tumor recurrence had not occurred, and the CEA titer was less than 2.5 ng/ml.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. A method for inducing a cellular immune response in a patient against a tumor that expresses carcinoembryonic antigen (CEA), said method comprising:
   administering an effective immunostimulatory amount of transfected T cells to a patient; and
   subsequently administering at least one cytokine to said patient;
   wherein said transfected T cells are produced by obtaining T cells from the patient and transfecting said T cells with an expression vector to obtain said transfected T cells;
   wherein said expression vector comprises a DNA molecule encoding either a chimeric immunoglobulin/T cell receptor or a chimeric immunoglobulin/CD3 protein, and wherein said immunoglobulin-encoding portion of said DNA molecule encodes the variable regions of a Class III anti-CEA antibody, wherein the Class III anti-CEA antibody is MN-14 or humanized MN-14, and further wherein the variable regions of the $\alpha$ and $\beta$ polypeptide chains of said T cell receptor are replaced by said variable regions of the antibody.

2. The method of claim 1, wherein the cytokine is selected from the group consisting of interferon-$\gamma$ and interleukin-2.

3. The method of claim 2, wherein said transfected T cells are stimulated ax vivo to obtain an increased mass of cells.

4. A method for inducing a cellular immune response in a patient against a tumor that expresses carcinoembryonic antigen (CEA), said method comprising:
   administering an effective immunostimulatory amount of transfected T cells to a patient; and
   subsequently administering at least one cytokine to said patient;
   wherein said T cells are produced by obtaining T cells from the patient and transfecting said T cells with an expression vector to obtain said transfected T cells;
   wherein said expression vector comprises a DNA molecule encoding either a chimeric immunoglobulin/T cell receptor or a chimeric immunoglobulin/CD3 protein, and wherein said immunoglobulin-encoding portion of said DNA molecule encodes the variable regions of an anti-idiotypic antibody that recognizes a Class III anti-CEA antibody, wherein the anti-idiotype antibody is WI2, and further wherein the variable regions of the $\alpha$ and $\beta$ polypeptide chains of said T cell receptor are replaced by said variable regions of the antibody.

5. The method of claim 4, wherein the cytokine is selected from the group consisting of interferon-$\gamma$ and interleukin-2.

6. The method of claim 4, wherein said transfected T cells are stimulated ex vivo to obtain an increased mass of cells.

* * * * *